(12) United States Patent
Yamaguchi et al.

(10) Patent No.: US 6,999,557 B2
(45) Date of Patent: Feb. 14, 2006

(54) METHOD OF SETTING MEASURING RANGE OF RECIPROCAL-SPACE MAPPING

(75) Inventors: Susumu Yamaguchi, Hamura (JP); Tetsuya Ozawa, Hino (JP); Katsuhiko Inaba, Ome (JP); Ryuji Matsuo, Ome (JP)

(73) Assignee: Rigaku Corporation, Akishima (JP)

( * ) Notice: Subject to any disclaimer, the term of this patent is extended or adjusted under 35 U.S.C. 154(b) by 31 days.

(21) Appl. No.: 10/854,563

(22) Filed: May 25, 2004

(65) Prior Publication Data

US 2004/0240611 A1      Dec. 2, 2004

(30) Foreign Application Priority Data

May 29, 2003 (JP) .............................. 2003-152772

(51) Int. Cl.
    *G01N 23/20*      (2006.01)

(52) U.S. Cl. .......................................... 378/71; 378/87
(58) Field of Classification Search ................. 378/70, 378/71, 87, 73, 80, 82, 72

See application file for complete search history.

(56) References Cited

U.S. PATENT DOCUMENTS

2003/0009316 A1    1/2003   Yokoyama et al.

FOREIGN PATENT DOCUMENTS

| EP | 0 959 345 A2 | 11/1999 |
|---|---|---|
| EP | 0959345 A2 * | 11/1999 |
| JP | 11-304729 | 11/1999 |
| JP | 2000-039409 A | 2/2000 |

OTHER PUBLICATIONS

B. D. Cullity, Elements of x-ray Diffraction, Second Edition, Japanese Version, Translated by G. Matsumura, Eight Reprinted Edition, Issued by Agune (1990) pp. 445-458.

B. D. Cullity, Elements of X-ray Diffraction, Addison-Wesley Publishing Company, Inc., (1956) pp. 490-505.

E. Koppensteiner et al: "Investigation of Strained-Symmetrized and Pseudomorphic Simgen Superlattices by X-Ray Reciprocal Space Mapping", Journal of Applied Physics, American Institute of Physics, New York, NY, US, vol. 76, No. 6, Sep. 15, 1994, pp. 3489-3501, XP000470066, ISSN: 0021-8979—p. 3490, Fig. 1.

C-H Chen et al: "Influence of Ultra-Thin YSZ Layer on Heteroepitaxial Ce02/YSZ/SI (001) Films Analyzed by X-Ray Reciprocal Space Map", Journal of Crystal Growth, North-Holland Publishing Co., Amsterdam, NL, vol. 219, No. 3, Oct. 15, 2000, pp. 253-262, XP004218356, ISSN: 0022-0248—p. 255.

(Continued)

*Primary Examiner*—David V. Bruce
*Assistant Examiner*—Hoon Song
(74) *Attorney, Agent, or Firm*—Frishauf, Holtz, Goodman & Chick, P.C.

(57) ABSTRACT

Reciprocal-space mapping measurement of X-ray diffraction requires setting of the measuring range of $2\theta/\omega$ and setting of the measuring range of $\omega$. When the measuring range of $\omega$ is designated in absolute angle, the absolute-angle-designated range is converted into a relative-angle-designated range to be acquired; preventing setting of a warped measuring region. When the measuring range of $\omega$ is designated in relative angle, it is acquired as it is. For the measuring range of $2\theta/\omega$, any one of the absolute-angle-designated range and the relative-angle-designated range may be acquired.

6 Claims, 16 Drawing Sheets

OTHER PUBLICATIONS

Bruker AXS GmbH: "Diffraction Solutions for Material Research—D8 Discover", Bruker Advanced X-Ray Solutions, 'Online! 1998, pp. 1-8, XP0002308273 Germany; Retrieved from the Internet: URL:http://www.bruker-axs.de/DocumentPool/Technical+Documents/Products+XRD/System+Brocures+1-5/D8+DISCOVER+Material+Research+English+low-res.pdf>—retrieved on Nov. 29, 2004!—entire document.

Database Inspec 'Online!, The Institute of Electrical Engineers, Stevenage, BG, E. P. Fewster: "Reciprocal Space Mapping", XP002308274, Database accession No. 5649095. —Abstract- and Critical Reviews in Solid State and Materials Sciences, vol. 22, No. 2, 1997, pp. 69-110, CRC Press, USA, ISSN: 1040-8436.

* cited by examiner

ω SCAN $2\theta/\omega$ SCAN

FIG. 14

A PART OF A CONDITIOIN-SETTING SCREEN

| | | | | |
|---|---|---|---|---|
| CENTER POINT | $2\theta/\omega$ | 60 | degree | |
| | $\omega$ | 30 | degree | |
| SCAN DIRECTION | ○ $2\theta/\omega$ SCAN | | | |
| | ⦿ $\omega$ SCAN | | | |
| SCAN METHOD | ○ CONTINUOUS SCAN | | | |
| | ⦿ STEP SCAN | | | |
| MEASURING RANGE | ⦿ RELATIVE ANGLE | | | |
| | ○ ABSOLUTE ANGLE | | | |
| | $2\theta/\omega$ | -10 ~ 10 | degree | |
| | $\omega$ | -10 ~ 10 | degree | |
| MEASURING INTERVAL | $2\theta/\omega$ | 0.1 | degree | |
| | $\omega$ | 0.1 | degree | |

FIG. 15

A PART OF A CONDITIOIN-SETTING SCREEN

| | | | | |
|---|---|---|---|---|
| CENTER POINT | $2\theta/\omega$ | 60 | degree | |
| | $\omega$ | 30 | degree | |
| SCAN DIRECTION | ○ $2\theta/\omega$ SCAN | | | |
| | ◉ $\omega$ SCAN | | | |
| SCAN METHOD | ○ CONTINUOUS SCAN | | | |
| | ◉ STEP SCAN | | | |
| MEASURING RANGE | ○ RELATIVE ANGLE | | | |
| | ◉ ABSOLUTE ANGLE | | | |
| | $2\theta/\omega$ | 50 ~ 70 | degree | |
| | $\omega$ | 20 ~ 40 | degree | |
| MEASURING INTERVAL | $2\theta/\omega$ | 0.1 | degree | |
| | $\omega$ | 0.1 | degree | |

METHOD OF SETTING MEASURING RANGE OF RECIPROCAL-SPACE MAPPING

BACKGROUND OF THE INVENTION

1. Field of the Invention

The present invention relates to a method of setting a measuring range in carrying out reciprocal-space mapping of X-ray diffraction measurement.

2. Description of the Related Art

The reciprocal-space mapping measurement is one of the measuring techniques of X-ray diffraction. First of all, a scattering vector will be explained before explanation of the reciprocal-space mapping. FIG. 1 is a view for explaining the scattering vector of X-ray diffraction, in which an X-ray 12 is incident on the surface of a sample 10, and a diffracted X-ray 14 goes out of the sample surface. An angle of the incident X-ray 12 to the surface of the sample 10 is referred to as an incident angle which is denoted by $\omega$, and an angle of the diffracted X-ray 14 to the incident angle 12 is referred to as a diffraction angle which is denoted by $2\theta$. In the X-ray diffraction measurement, the incident X-ray 12 comes from an X-ray source 16, and the diffracted X-ray 14 is to be detected by an X-ray detector 18.

An X-ray diffraction phenomenon will be explained with the use of the reciprocal space of the crystal which makes up the sample 10. A unit vector $S_0$ is taken as extending in the direction of the incident X-ray 12, and another unit vector S is taken as extending in the direction of the diffracted X-ray 14. Assuming that an incident X-ray vector is defined as $S_0/\lambda$ and a diffracted X-ray vector is defined as $S/\lambda$ where $\lambda$ is the wavelength of an X-ray, vectorial subtraction of the incident X-ray vector from the diffracted X-ray vector becomes, as well known, the scattering vector H. The X-ray diffraction principle suggests that when the tip location of the scattering vector H coincides with any lattice point in the reciprocal space, X-ray diffraction occurs at the real lattice plane 20, which is a crystal lattice plane in the real space, corresponding to the reciprocal lattice point. The scattering vector H has the property that the direction is perpendicular to the real lattice plane 20 and the magnitude is equal to the inverse number of the lattice spacing of the real lattice plane 20. The direction of the scattering vector H can be expressed by a tilt angle $\alpha$ to the normal 22 of the surface of the sample 10 within a plane including the incident X-ray 12 and the diffracted X-ray 14.

The reciprocal-space mapping is defined as how the X-ray diffraction intensity varies with $\omega$ and $2\theta$. The mapping can be obtained with the procedure in which the incident angle $\omega$ and the diffraction angle $2\theta$ are changed so as to change the direction and the magnitude of the scattering vector within a desired range and the X-ray diffraction measurement is carried out for each scattering vector. How the scattering vector varies with $\omega$ and $2\theta$ will be explained below.

FIG. 2 is an explanatory view of the direction change of the scattering vector H with the magnitude unchanged. The incident X-ray vector will be referred to as simply the incident X-ray 12 and the diffracted X-ray vector will be referred to as simply the diffracted X-ray 14 in the description below. It is assumed that the incident angle $\omega$ of the incident X-ray 12 is increased by $\Delta\omega$, that is clockwise turning in FIG. 2, and the direction of the diffracted X-ray 14, i.e., the angular location of an X-ray detector, is changed by $\Delta\omega$ in the same turning direction. In this case, the direction of the scattering vector H changes while the diffraction angle $2\theta$ does not change. The tilt angle $\alpha$ becomes $\alpha+\Delta\omega$. Thus, if the incident X-ray 12 and the diffracted X-ray 14 are changed in the same turning direction by the same angle as described above, only the direction of the scattering vector H changes. This movement with such angular changes is referred to as an $\omega$ scan.

Another scanning method will be explained with reference to FIG. 3 which is an explanatory view of the magnitude change of the scattering vector H with the direction unchanged. When the diffracted X-ray 14 is turned counterclockwise in FIG. 3 by a certain angle, which equals to $\Delta 2\theta/2$, and the incident X-ray 12 is turned inversely, i.e., clockwise in FIG. 3, by the same angle, the diffraction angle $2\theta$ is changed to $2\theta+\Delta 2\theta$ and the incident angle $\omega$ is changed to $\omega+\Delta 2\theta/2$. Thus, if the directions of the incident X-ray and the diffracted X-ray are changed inversely as described above, only the magnitude of the scattering vector H changes with the direction unchanged. This movement with such angular changes is referred to as a $2\theta/\omega$ scan.

An operation of the $\omega$ scan brings only an $\omega$ change with $2\theta$ unchanged, while an operation of the $2\theta/\omega$ scan brings a $2\theta$ change along with an $\omega$ change which is a half of the $2\theta$ change. The property of the $2\theta/\omega$ scan described above deeply concerns the problem between the designation of the relative angle and the designation of the absolute angle in the present invention.

FIG. 4 shows the movement of the scattering vector in the reciprocal space in the $\omega$ scan. Each of the tip location of the scattering vector is represented by a black dot, which is referred to hereinafter as a measuring point. Each operation of X-ray diffraction measurement is to be carried out at each black dot. The center position of the measuring range, i.e., the center position of the reciprocal-space mapping, is assumed to be located at a point O. When the $\omega$ scan is carried out with the magnitude of the scattering vector kept the same as that at the point O, the measuring point moves from a point A to a point B. The $\omega$ varies from a smaller value to a larger value in the scan. The measuring point in the case moves circumferentially centering on the X-ray irradiation point on the sample 10. If it is desired to change the magnitude of the scattering vector to another value for another $\omega$ scan, the measuring point is moved, for example, from the point O to a point C, that is the magnitude of the scattering vector is decreased so that $2\theta/\omega$ is changed by a certain value. Then the $\omega$ scan is carried out with the magnitude of the scattering vector kept the same as that at the point C, i.e., the measuring point moves from a point E to a point F. In the actual procedure, the magnitude of the scattering vector, which corresponds to the value of $2\theta/\omega$, is changed stepwise at certain measuring intervals from the point C to a point D, and the $\omega$ scan is carried out for each magnitude of the scattering vector. FIG. 4 shows, for easier understanding, five values of the magnitude of the scattering vector and thus five kinds of the $\omega$ scan. An operation of X-ray diffraction measurement is carried out, in each $\omega$ scan, at the five measuring points with the direction of the scattering vector different from each other, obtaining twenty-five measured results. It is noted, however, that a larger number of measuring points would be selected generally in the actual reciprocal-space mapping measurement.

FIG. 5 shows the movement of the scattering vector in the reciprocal space in the $2\theta/\omega$ scan. Five kinds of the direction, which correspond to the value of $\omega$, of the scattering vector are selected in this case and thus five kinds of the $2\theta/\omega$ scan are carried out. The measuring point in the $2\theta/\omega$ scan moves on a line passing through the X-ray irradiation point on the sample 10, because the 2θ/ω scan brings the change of the magnitude of the scattering vector with the direction kept constant.

The explanation about the measuring points having been described above is done with the reference to the reciprocal space, and thus the explanation would be clear. Actual measuring conditions, however, must be designated with the use of the incident angle ω and the diffraction angle 2θ. The measuring range of ω in the ω scan may be designated in either relative angle or absolute angle, affecting the shape of the measuring region as shown in FIG. 4 indicating a fair shape of the measuring region and in FIG. 6 indicating a warped shape of the measuring region. The two measuring regions different from each other will be described in detail below.

FIG. 7 is a graph expressing a measuring region for the ω scan shown in FIG. 4 in the coordinate system made of ω-axis and 2θ/ω-axis. The meaning of 2θ/ω, which is used as ordinate, is an angle 2θ in the case where 2θ and ω are changed in the interlocking fashion in the 2θ/ω scan. The central measuring point O of the reciprocal-space mapping is assumed to be 60 degrees in 2θ/ω and 30 degrees in ω. The angle 2θ/ω is assumed to vary within a range of ±10 degrees and ω is assumed to vary within a range of ±10 degrees too on the basis of the central measuring point O. When ω is scanned within a range of ±10 degrees with the magnitude of the scattering vector kept constant, i.e., 2θ is constant, on the basis of the measuring point O, the measuring point moves from a point A to a point B. The measuring conditions have the five points: 20, 25, 30, 35 and 40 degrees in ω and 60 degrees in 2θ/ω which is kept constant. The angle ω is thus to vary from 20 to 40 degrees.

When it is desired to carry out another ω scan for another value of 2θ/ω, the magnitude of the scattering vector may be changed from the measuring point O with the direction unchanged, i.e., the tilt angle α is unchanged as shown in FIG. 3. For example, the measuring point jumps from the point O into a point C, 50 degrees in 2θ/ω, and the ω scan is carried out with ω varying within a range of ±10 degrees for this value of 2θ/ω. It should be noted, in this case, that when the measuring point moves from the point O to the point C with the angle α kept constant, the angle 2θ is decreased by 10 degrees and further the angle ω is also decreased by 5 degrees in accordance with the decrease of 2θ. The location of the point C is thus 25 degrees in ω. When the angle ω is changed from the point C within a range of ±10 degrees, the angle ω is to vary between 15 degrees, a point E, and 35 degrees, a point F. It will be seen accordingly that the measuring range between 20 and 40 degrees in ω in the case of 60 degrees in 2θ/ω is indeed different from the measuring range between 15 and 35 degrees in ω in the case of 50 degrees in 2θ/ω. A similar situation will occur in the case of every change of 2θ/ω. After all, as shown in FIG. 11, the measuring range becomes within a range of ±10 degrees in ω centering on a line 24 which is constant in α on the basis of the measuring point O.

Although FIG. 11 shows a graph whose abscissa represents an absolute angle of ω, the absolute angle may be replaced with, as shown in FIG. 9, a relative angle Δω measured from the line 24 (see FIG. 11) which is constant in α. It will be seen that the measuring region in FIG. 9 becomes a fair shape. Therefore, if the measuring range of the ω scan is designated by the relative angle Δω, ±10 degrees in the case above, the measuring region with a fair shape such as shown in FIG. 9 and FIG. 4 can be produced.

Incidentally, there exists a certain apparatus in which the measuring range in ω can be designated with the use of selectively the relative angle or the absolute angle on the setting screen for the measuring conditions of the reciprocal-space mapping. If the measuring range in ω is designated in relative angle, it brings a situation such as shown in FIG. 12. The measuring range in ω can be designated with 20 and 40 degrees: the 20-degree value is 10 degrees lower than the center point O which is 30 degrees in ω, and the 40-degree value is 10 degrees higher than the center point O. It would be no problem when 2θ/ω is 60 degrees. However, there is a problem when 2θ/ω is 50 degrees for example, in which the minimum value in ω is 20 degrees which is minus 5 degrees measured from the point C and the maximum value in ω is 40 degrees which is plus 15 degrees measured from the point C. Although the measuring range is selected to range from 20 to 40 degrees in absolute angle, this measuring range is defined to range from minus 5 to plus 15 degrees in relative angle measured from the point C. Such a measuring range may be expressed, in the reciprocal space, with a line of the ω scan passing through the point C in FIG. 6. Comparing the measuring range in FIG. 6 with the measuring range in FIG. 4, the scan range in ω takes a rightward shift. Assuming that the whole measuring region is transferred in the reciprocal space, it becomes a shaded region shown in FIG. 6. The designation of the measuring range in ω with the use of the absolute angle would bring such a warped measuring range disadvantageously. The abscissa of the graph shown in FIG. 12 can be replaced with Δω so as to make a graph shown in FIG. 13, from which it is seen that the measuring range in Δω takes a different shift depending upon the value of 2θ/ω.

If an operator dares to designate the measuring range in ω with the use of the absolute angle with the understanding of the measuring region such as shown in FIG. 6, i.e., the measuring region in Δω as shown in FIG. 13, in the setting operation for the measuring conditions of the reciprocal-space mapping, it would be no problem. It would be considered, however, that the reciprocal-space mapping measurement with the measuring region such as shown in FIG. 6 has no merit. It is presumed accordingly that the operator would think, without careful consideration, the measuring regions are similar to each other between the two types of designation with the use of the relative angle and the absolute angle. Using the measuring region shown in FIG. 6, the data processing after the measurement must be changed as compared with the case with the measuring region shown in FIG. 4. If the measured result is obtained indeed with the measuring region shown in FIG. 6 but the operator misinterprets that the result is obtained with the measuring region shown in FIG. 4, the data processing would have trouble.

There is some merit to suggestions therefore that the designation in absolute angle should be impossible on the setting screen. There are some cases, however, that the designation in absolute angle is more helpful in understanding the region to be measured than in relative angle. Eventually there exists at present a certain apparatus which makes it possible to designate the measuring range in ω with the use of both the relative angle and the absolute angle selectively.

It is noted that, in setting the measuring range in 2θ/ω, the measuring regions become the same as each other between the designation in relative angle and absolute angle. This will be explained below.

FIG. 10 shows the movement of the 2θ/ω scan in the coordinate system with Δω, which is the relative angle, in abscissa and 2θ/ω in ordinate. The angle 2θ/ω is to move always from 50 to 70 degrees whatever Δω is. The measuring regions in this case become the same as each other between the designation in relative angle and in absolute angle.

FIG. 8 shows a graph which is obtained by a conversion in which operation that the abscissa of the graph shown in FIG. 10 is replaced with ω which is the absolute angle. When the 2θ/ω scan is carried out along any line which is kept constant in α, the angle 2θ/ω is to move always from 50 to 70 degrees. It is seen, from both FIG. 10 and FIG. 8, that even if the expression of 2θ/ω in ordinate is changed from the absolute angle to the relative angle which is Δ2θ/ω centering on 60 degrees, the measuring region will remain as it is.

The prior art against the present invention is disclosed in the following publications: B. D. Cullity, Elements of X-ray Diffraction, Second Edition, Japanese Version, Translated by G. Matsumura, Eighth Reprinted Edition, Issued by Agune (1990) page 445–458, referred to hereinafter as the first publication; Japanese Patent Publication No. 2000-39409 A (2000), referred to hereinafter as the second publication; and Japanese Patent Publication No. 11-304729 A (1999), referred to hereinafter as the third publication. The explanation of the X-ray diffraction phenomenon using the scattering vector is disclosed in the first publication. The reciprocal-space mapping measurement is disclosed in the second and the third publications, which do not mention the difference between the relative angle and the absolute angle in setting the measuring range of the reciprocal-space mapping.

SUMMARY OF THE INVENTION

It is an object of the present invention to provide a method of setting a measuring range of reciprocal-space mapping, which can prevent setting of a warped measuring region such as one shown in FIG. 6 mentioned above.

The present invention relates to a method of setting a measuring range in obtaining a reciprocal-space mapping of X-ray diffraction. The reciprocal-space mapping can be obtained as follows: there is prepared a first angular variable and a second angular variable both of which define a relative angular location among an incident X-ray, a sample and a diffracted X-ray; the first angular variable is changed so as to change a magnitude of a scattering vector of X-ray diffraction with its direction kept constant, so that a first condition-change is produced; the second angular variable is changed so as to change the direction of the scattering vector of X-ray diffraction with its magnitude kept constant, so that a second condition-change is produced; the first condition-change and the second condition-change are combined with each other so as to make a plurality of the scattering vectors which are included in a desired measuring region surrounding a predetermined target point in a reciprocal space; and X-ray diffraction measurement is carried out for the thus-determined scattering vectors so as to make the reciprocal-space mapping.

A method of setting the measuring range for making such a reciprocal-space mapping according to the present invention comprises the steps of: (a) determining whether a designated range of the second angular variable is a relative-angle-designated range on a basis of the target point or an absolute-angle-designated range; (b) acquiring the relative-angle-designated range as an allowable range of the second angular variable when the determining step determines the relative-angle-designated range, or converting the absolute-angle-designated range into the relative-angle-designated range and acquiring the thus-converted relative-angle-designated range when the determining step determines the absolute-angle-designated range; and (c) acquiring any one of a relative-angle-designated range and an absolute-angle-designated range as an allowable range of the first angular variable.

The present invention has an advantage that if an operator designate an allowable range of the second angular variation with the use of the absolute angle, the absolute-angle-designated range is converted into a relative-angle-designated range, so that the measuring regions are the same as each other between the relative-angle designation and the absolute-angle designation, preventing setting of a warped measuring region such as shown in FIG. 6.

BRIEF DESCRIPTION OF THE DRAWINGS

FIG. 14 shows an example of a display screen indicating a part of a condition-setting screen for the reciprocal-space mapping;

FIG. 15 shows an example of a display screen indicating another state of the condition-setting screen shown in FIG. 14.

DESCRIPTION OF THE PREFERRED EMBODIMENTS

An embodiment of the present invention will be described with reference to the drawings. The various drawings mentioned above in the description of the related art are usable as they are in the description of the embodiment of the present invention, and thus the embodiment will described with the reference to those drawings too.

FIG. 14 shows a part, relating to the present invention only, of a condition-setting screen for the reciprocal-space mapping. The condition-setting screen includes a "center point" item, a "scan direction" item, a "scan method" item, a "measuring range" item, and a "measuring interval" item.

Figure 1:
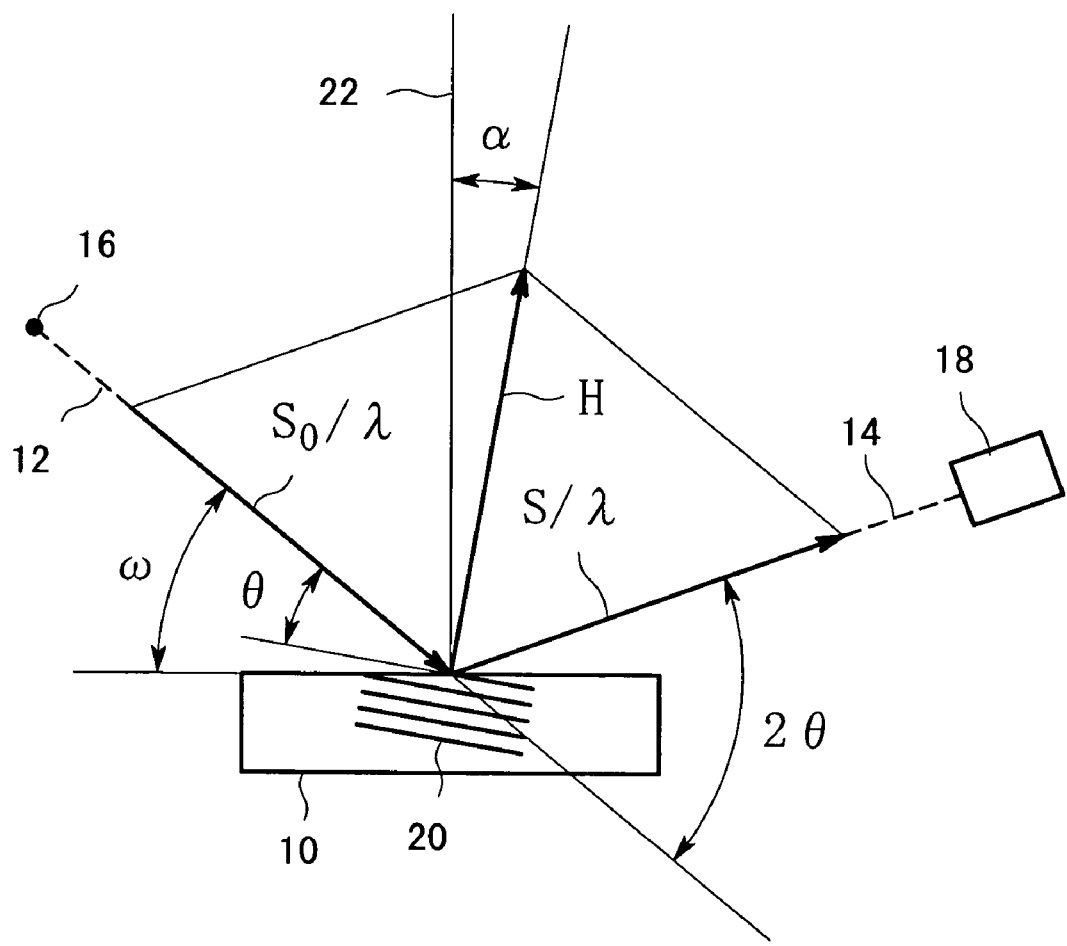
FIG. 1 is an explanatory view of the scattering vector of X-ray diffraction.
Figure 2:
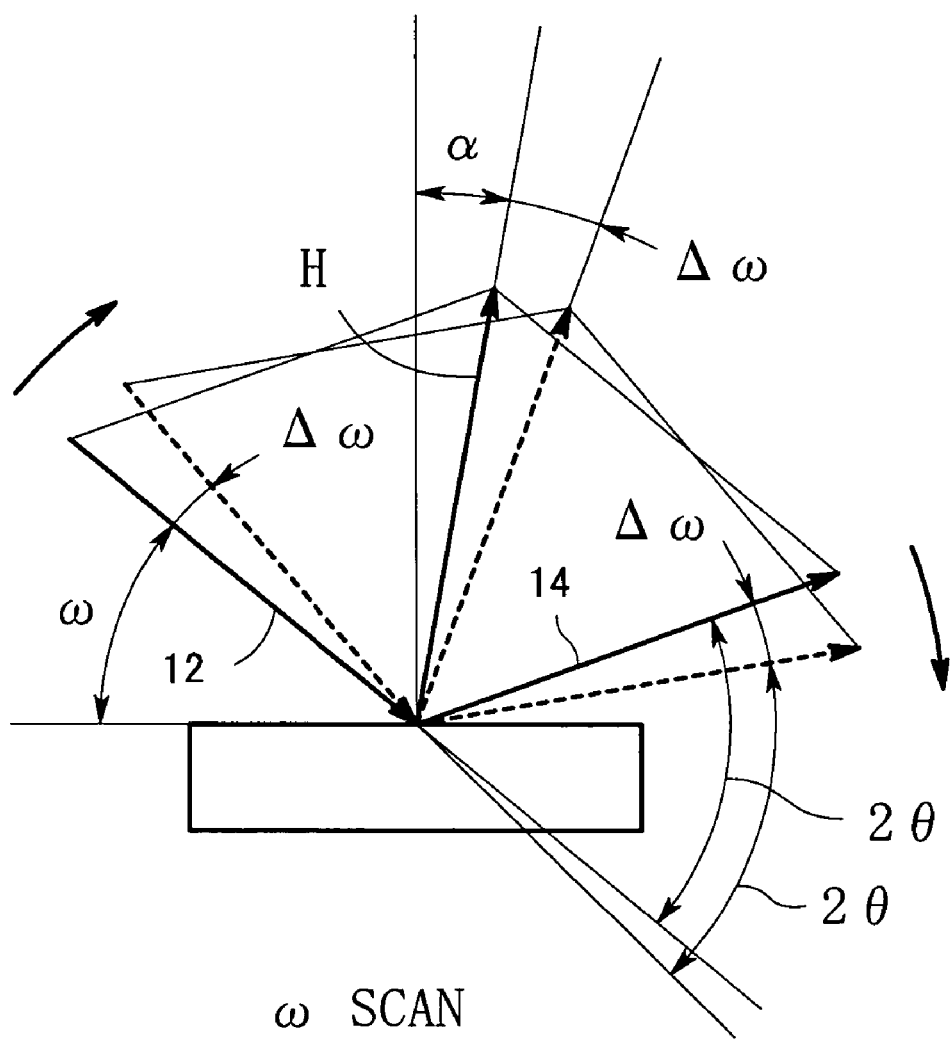
FIG. 2 is an explanatory view of the direction change of the scattering vector with the magnitude unchanged.
Figure 3:
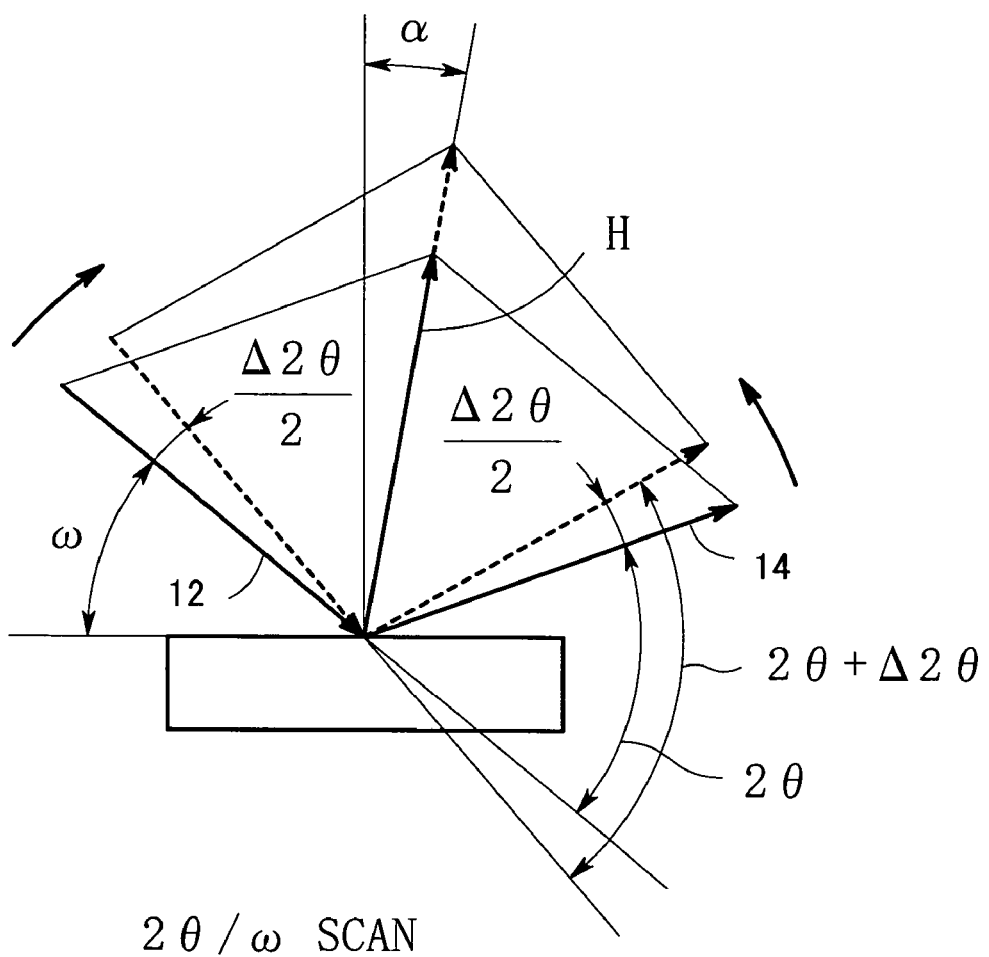
FIG. 3 is an explanatory view of the magnitude change of the scattering vector with the direction unchanged.
Figure 4:
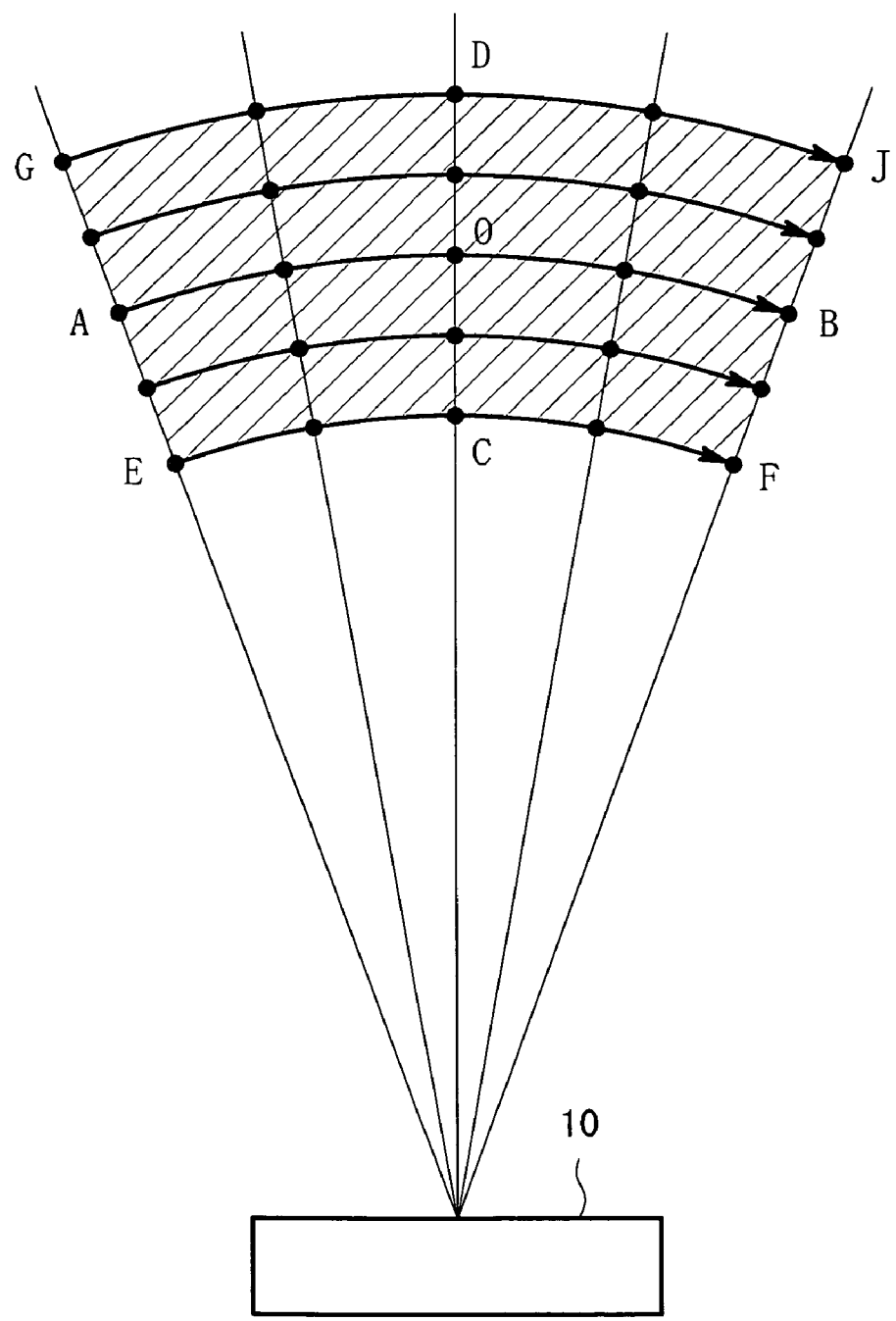
FIG. 4 is an explanatory view showing the movement of the scattering vector in the ω scan in the reciprocal space.
Figure 9:
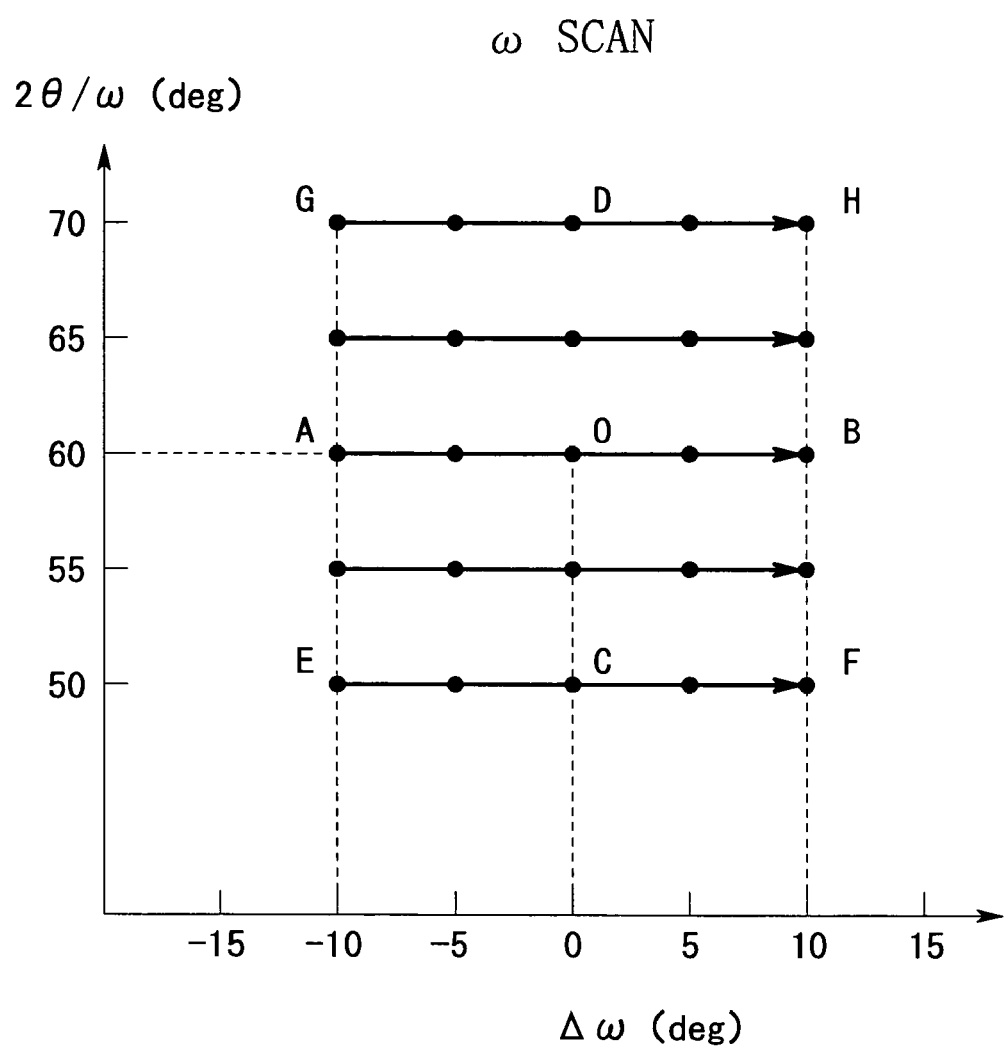
FIG. 9 is a graph expressing a measuring range for the ω scan in the coordinate system made of Δω-axis and 2θ/ω-axis.
Figure 10:
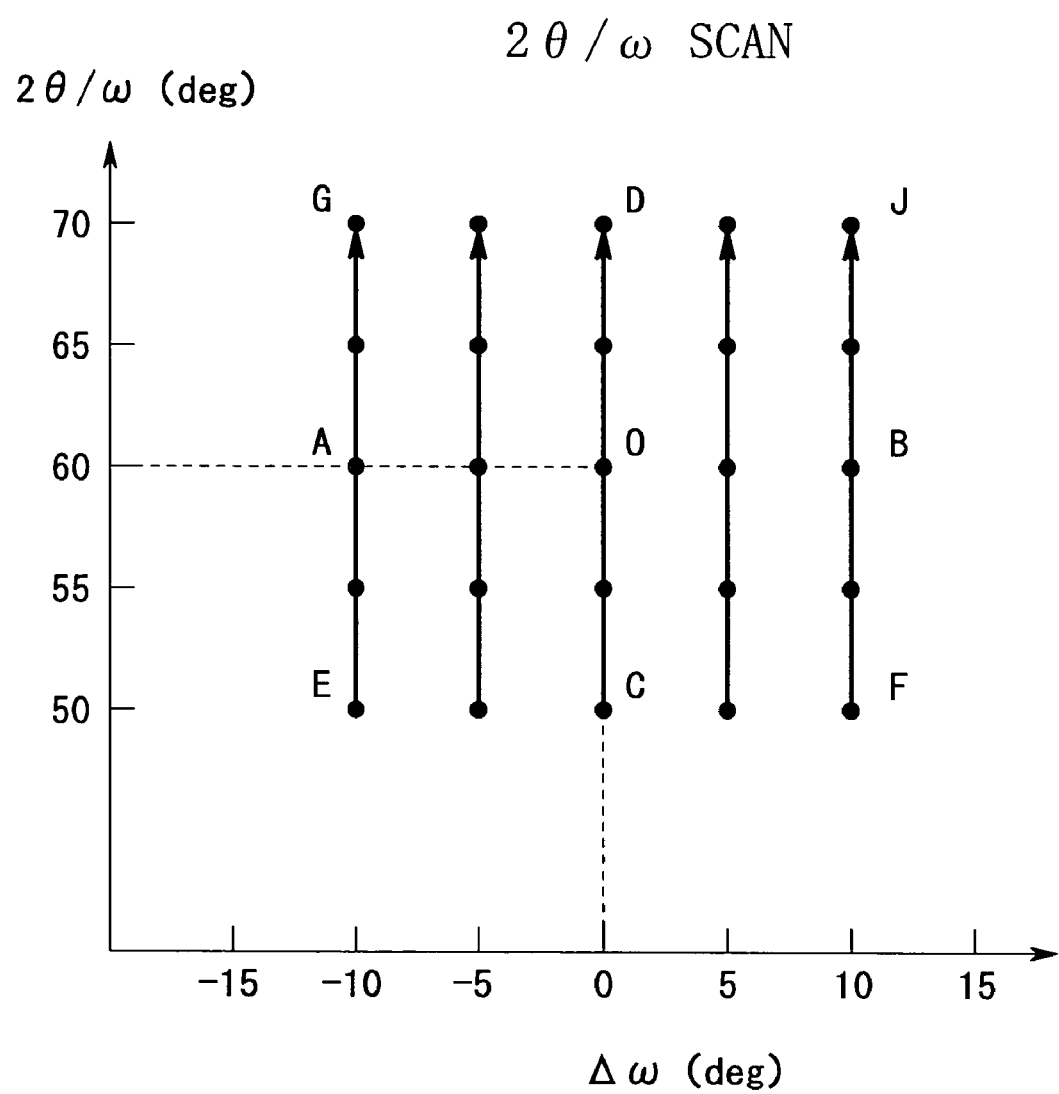
FIG. 10 is a graph expressing a measuring range for the 2θ/ω scan in the coordinate system made of Δω-axis and 2θ/ω-axis.
Figure 11:
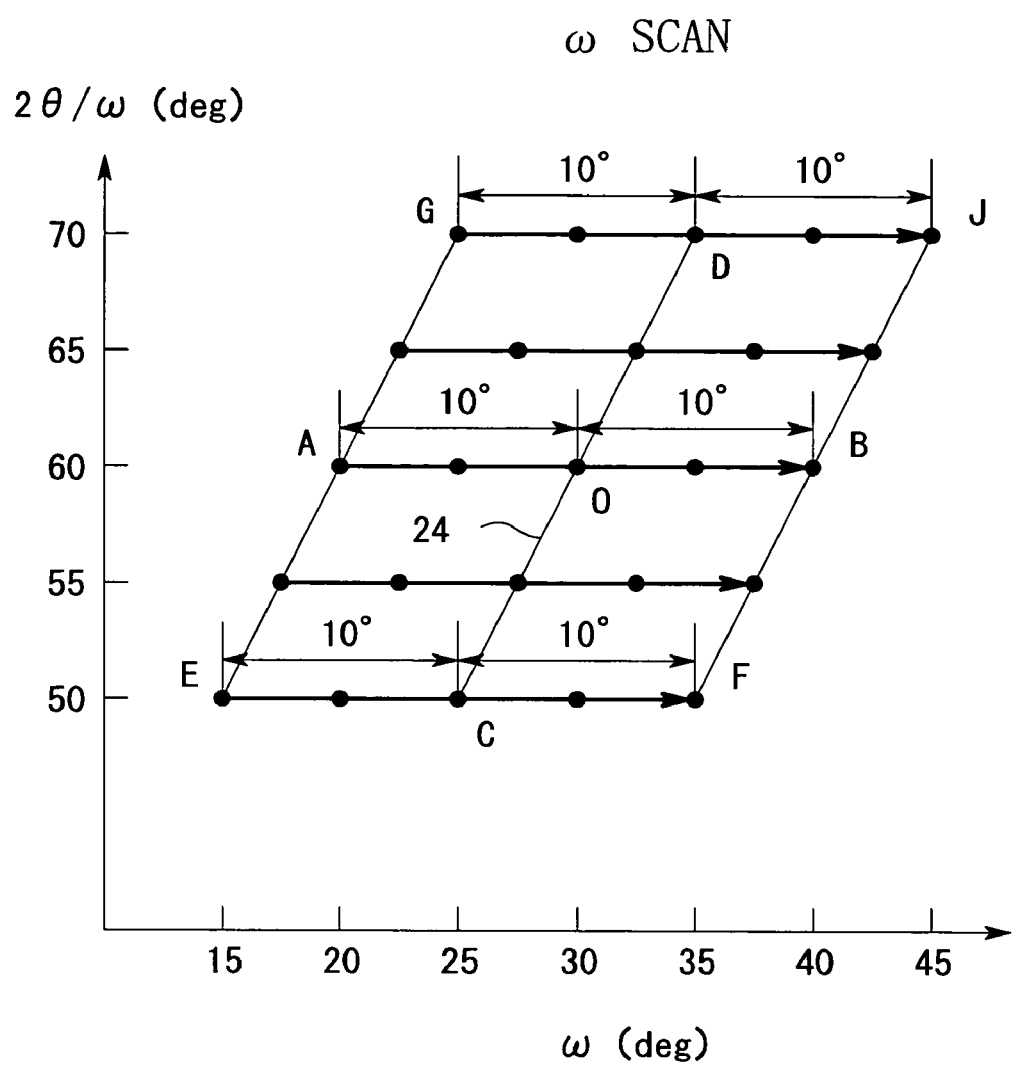
FIG. 11 is another graph expressing a measuring range for the ω scan in the coordinate system made of ω-axis and 2θ/ω-axis.

The "center point" means the designated values in 2θ/ω and ω of the center point O which is seen for example in FIGS. 4 and 9. An operator can enter, into two boxes in the "center point", angles of the center point of a measuring region with which the operator wants to carry out the reciprocal-space mapping measurement. FIG. 14 shows the state in which 60 degrees was entered into the 2θ/ω box and 30 degrees was entered into the ω box. It is noted that the 2θ/ω corresponds to the first angular variable in the present invention, the ω corresponds to the second angular variable in the present invention, and the center point corresponds to the target point in the present invention.

Figure 5:
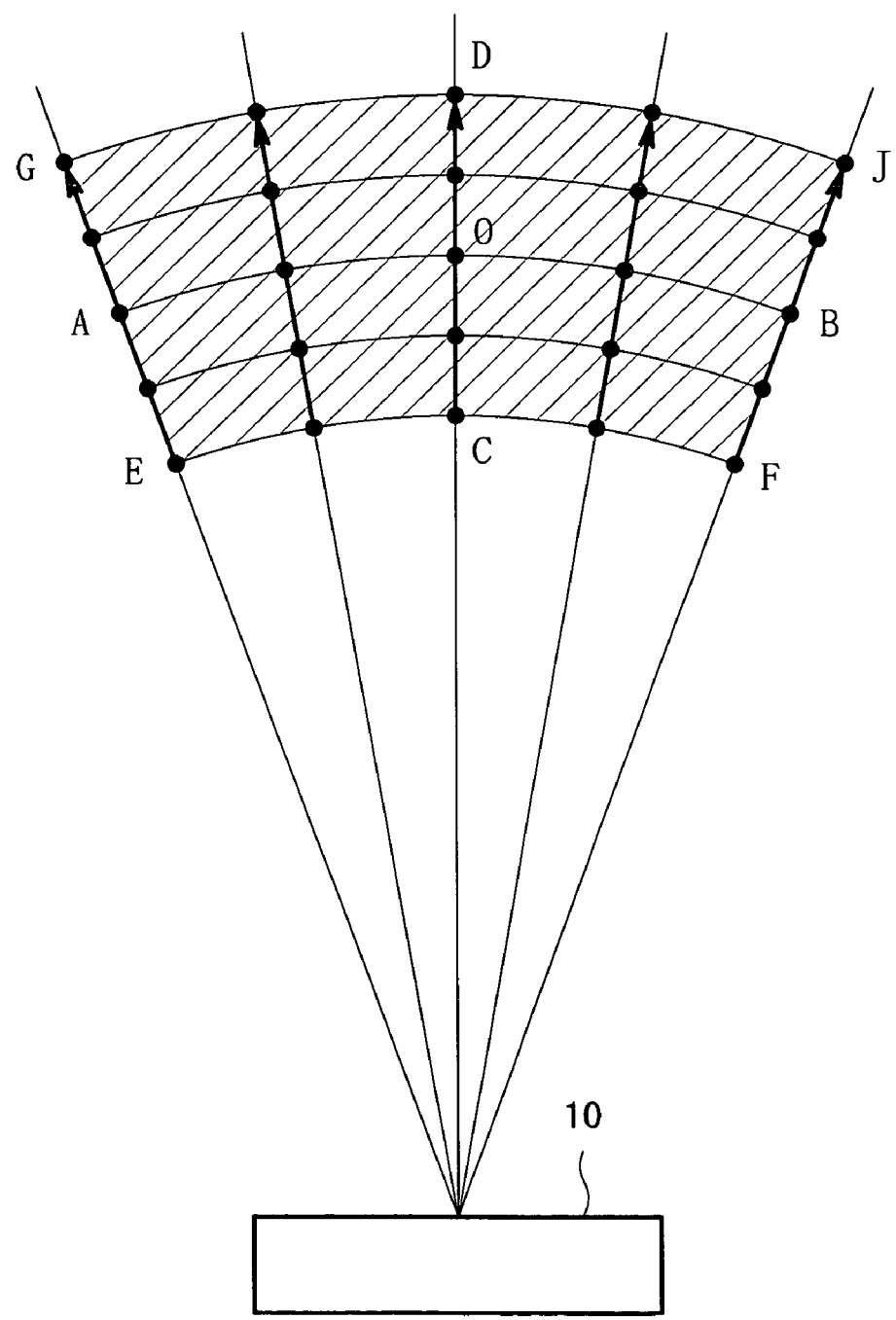
FIG. 5 is an explanatory view showing the movement of the scattering vector in the 2θ/ω scan in the reciprocal space.

The "scan direction" determines which is selected the 2θ/ω scan as shown in FIG. 5 or the ω scan as shown in FIG. 4. When the 2θ/ω scan is selected, the measurement process is that ω is changed stepwise at certain-angle intervals and the 2θ/ω scan is carried out for each ω value. When the ω scan is selected, the measurement process is that 2θ/ω is changed stepwise at certain-angle intervals and the ω scan is carried out for each 2θ/ω value. FIG. 14 shows the state in which the ω scan was selected. It is noted that the 2θ/ω scan corresponds to the first condition-change in the present invention, while the ω scan corresponds to the second condition-change in the present invention.

The "scan method" determines which is selected the continuous scan or the stepwise scan. The continuous scan is defined as to carry out each operation of the X-ray diffraction measurement during a continuous change in angle to be scanned. In contrast, the stepwise scan is defined as to carry out each operation of the X-ray diffraction measurement at a temporarily stationary angle to be scanned. In the case of the continuous scan, the obtained X-ray diffraction intensity should be taken as the data at the center position of the angle which changes during the measurement operation.

The "measuring range" item has a selection region and an entry region. An operator can mark one of two check places in the selection region to select the relative angle or the absolute angle as an entry mode for numerical values. The operator then can enter numerical values into two entry boxes for 2θ/ω and two entry boxes for ω in the entry region in accordance with the entry mode selected. FIG. 14 shows the state the relative angle was selected, a range from minus 10 degrees to plus 10 degrees was designated in 2θ/ω, and a range from minus 10 degrees to plus 10 degrees was designated in ω. The thus-designated measuring range is the same as one shown in FIG. 9.

The "measuring interval" means the angular interval at which the measurement operations are carried out. FIG. 14 shows the state that a 0.1-degree interval was designated in 2θ/ω and a 0.1-degree interval was designated in ω too.

When the measurement is carried out under the measuring conditions shown in FIG. 14, the 2θ/ω is selected from 50 degrees, which is sixty minus ten degrees, to 70 degrees, which is sixty plus ten degrees, at 0.1-degree intervals, running up two-hundred setting points in 2θ/ω. The stepwise ω scan is carried out for each setting point with ω ranging from minus 10 degrees to plus 10 degrees at 0.1-degree intervals, and an operation of X-ray diffraction measurement is carried out for each ω value. After all, the frequency of the measurement operations runs up in total two-hundred times two-hundred being forty thousands. It should be noted, however, that the measuring conditions described above are virtual and the actual conditions would have smaller angular ranges and may have various measuring intervals depending upon the purpose of measurement.

Figure 6:
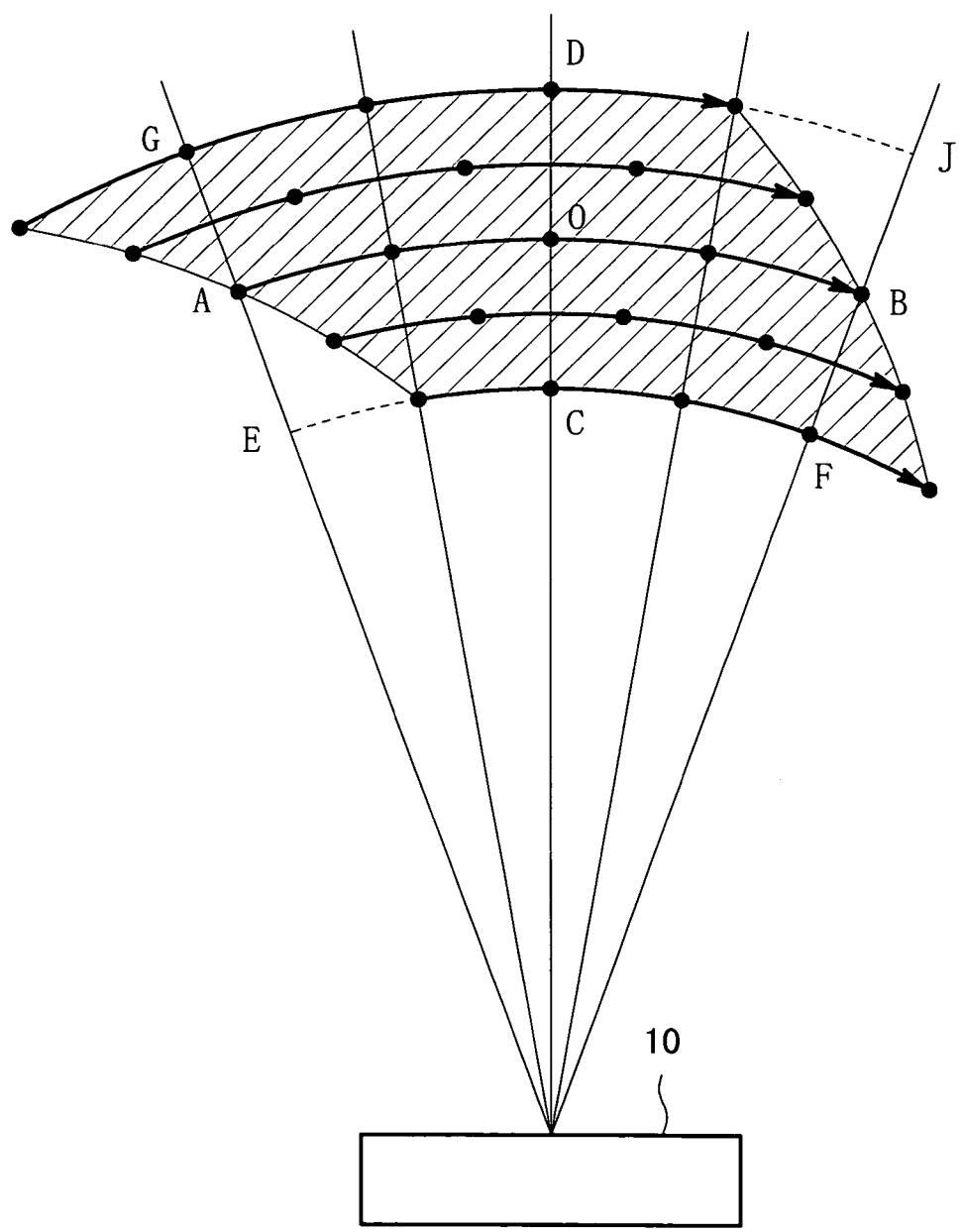
FIG. 6 is an explanatory view showing a warped measuring region.

Although the measuring range is designated with the use of the relative angle in FIG. 14, the measuring range may be designated with the use of the absolute angle as shown in FIG. 15. The conditions shown in FIG. 15 are different from those in FIG. 14 in that the absolute angle was selected in the "measuring range" term and, in accordance with the selection, the numerical values of 50 and 70 were entered into the 2θ/ω boxes and 20 and 40 were entered into the ω boxes. With the designated conditions shown in FIG. 15, the measuring range shown in FIG. 12, i.e., the measuring region shown in FIG. 6, would be produced in the prior art, because the measuring range for the ω scan was designated in absolute angle. In contrast, the present invention provides the situation that when the absolute angle was selected in the "measuring range" term, the absolute-angle-designated range is converted into a relative-angle-designated range in the control device which governs the measuring conditions of the reciprocal-space mapping. That is, the designated conditions shown in FIG. 15 are automatically converted into the conditions shown in FIG. 14. Accordingly, even if an operator enters the measuring conditions shown on the setting screen in FIG. 15, the designated measuring conditions indeed become the same as those shown on the setting screen in FIG. 14 inside the control device, preventing setting of a warped measuring region as shown in FIG. 6 and assuring a fine measuring region as shown in FIG. 4.

Figure 16:
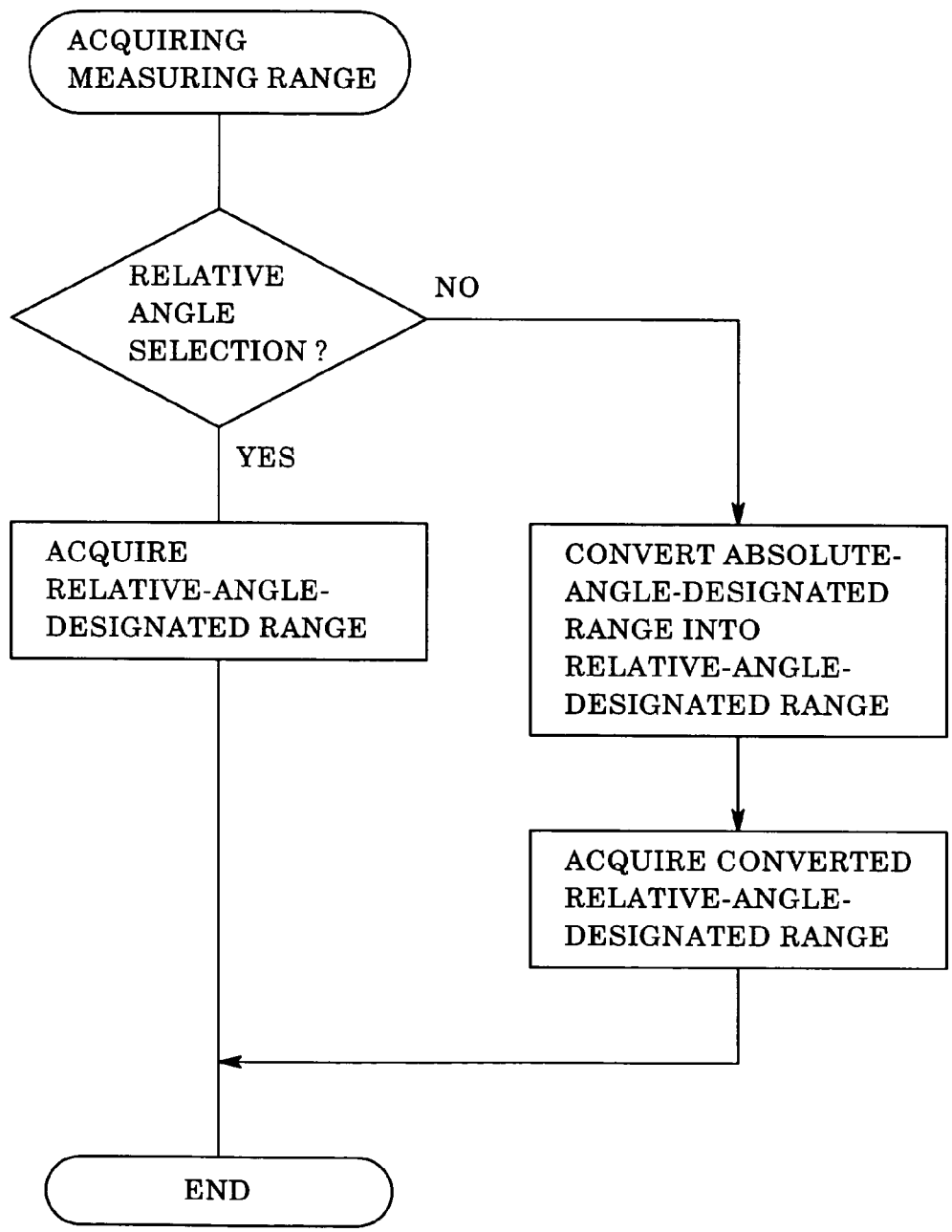
FIG. 16 is a flow chart of the process for acquiring the measuring range.

FIG. 16 is a flow chart of the process for acquiring the measuring range. First, the control device determines whether the relative angle is selected or the absolute angle is selected in the "measuring range" term on the condition-setting screen shown in FIG. 14. When determining the relative angle, the control device acquires the numerical range of 2θ/ω and the numerical range of ω as allowable measuring ranges, these numerical values being in relative angle. In contrast, when determining the absolute angle, the control device acquires temporarily the numerical range of 2θ/ω and the numerical range of ω, these numerical values being in absolute angle, and converts those values into numerical values in relative angle, and finally acquires the converted relative-angle ranges as allowable measuring ranges.

Although the process described above converts all the values in absolute angle for both 2θ/ω and ω into the values in relative angle, the control device may acquire the values in absolute angle for 2θ/ω as it is as an allowable measuring range, because the measuring regions become the same as each other between the relative-angle-designation and the absolute-angle-designation for 2θ/ω. The process for acquiring the measuring range accordingly may be carried out such that the designated numerical values for 2θ/ω are acquired as they are similarly to the prior art, while the designated numerical values for ω are acquired in accordance with the flow chart shown in FIG. 16.

The operation of the step "convert absolute-angle-designated range into relative-angle-designated range" may be carried out with any one of the following two kinds of methods. The first method is that the absolute-angle-designated values are converted into the relative-angle-designated values and the control device acquires the thus-converted values so as to do the same control as in the case in which the control device acquires the relative-angle-designated values. This method is equivalent to conversion of the setting screen shown in FIG. 15 into the setting screen shown in FIG. 14 inside the control device.

Figure 7:
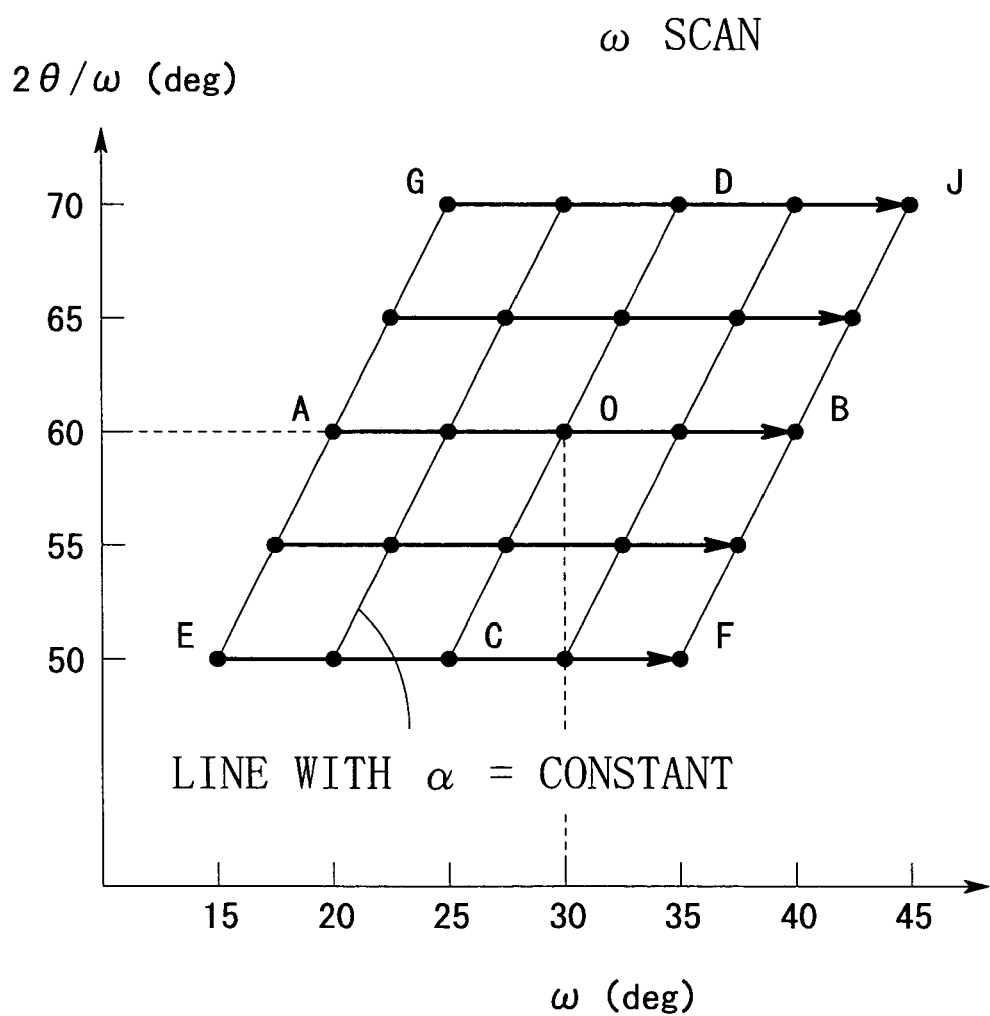
FIG. 7 is a graph expressing a measuring range for the ω scan shown in FIG. 4 in the coordinate system made of ω-axis and 2θ/ω-axis.
Figure 8:
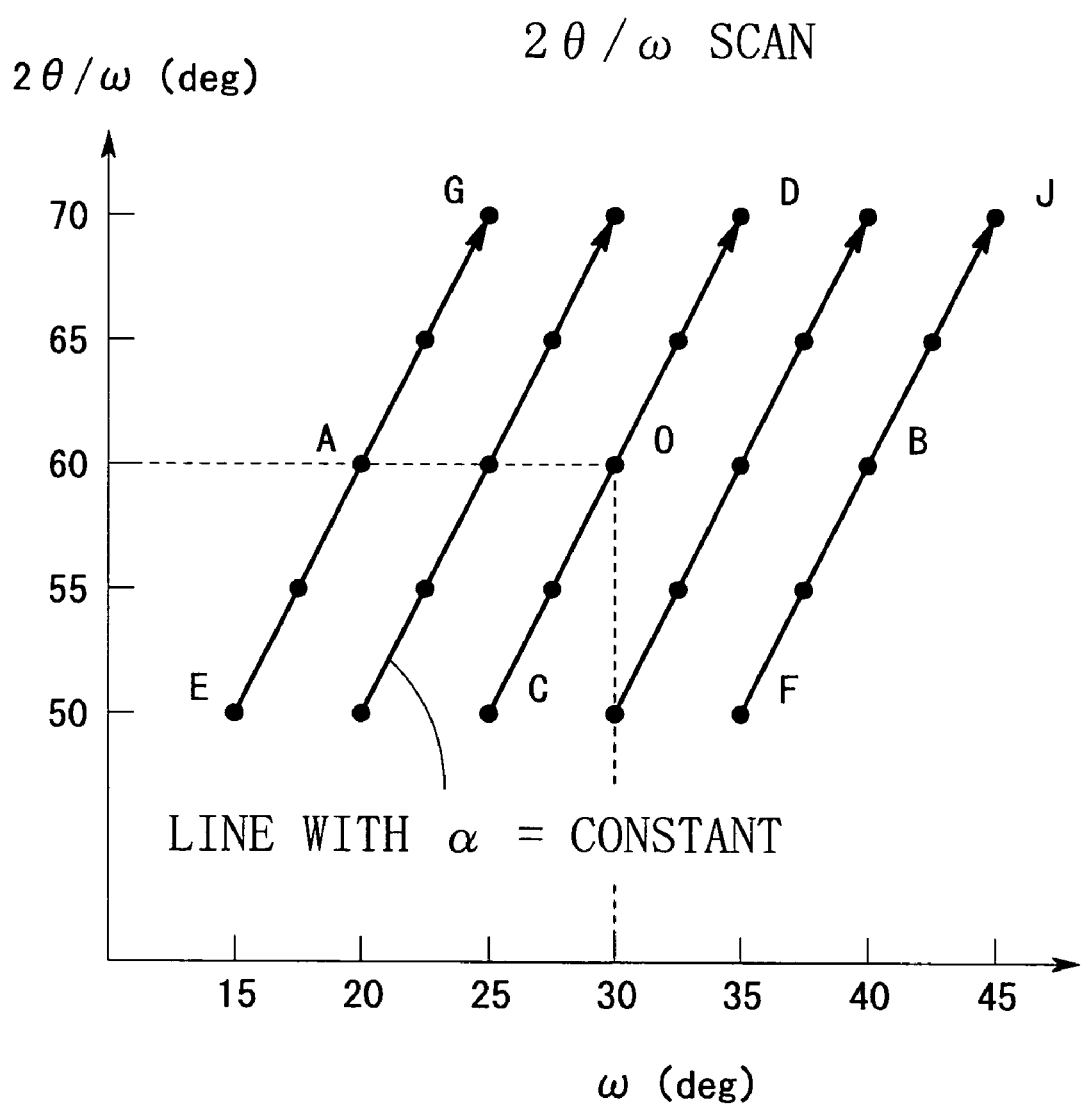
FIG. 8 is a graph expressing the measuring range shown in FIG. 10 in the coordinate system made of ω-axis and 2θ/ω-axis.
Figure 12:
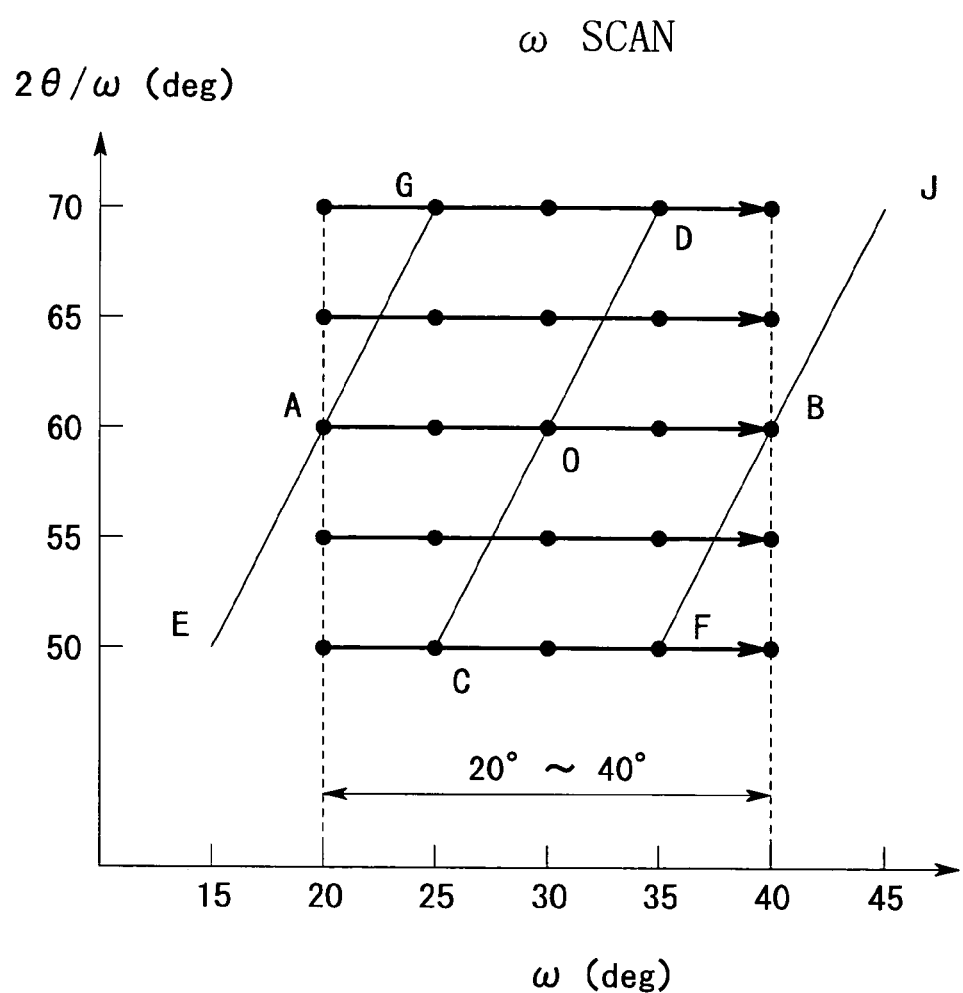
FIG. 12 is another graph expressing an absolute-angle-designated measuring range for the ω scan in the coordinate system made of ω-axis and 2θ/ω-axis.
Figure 13:
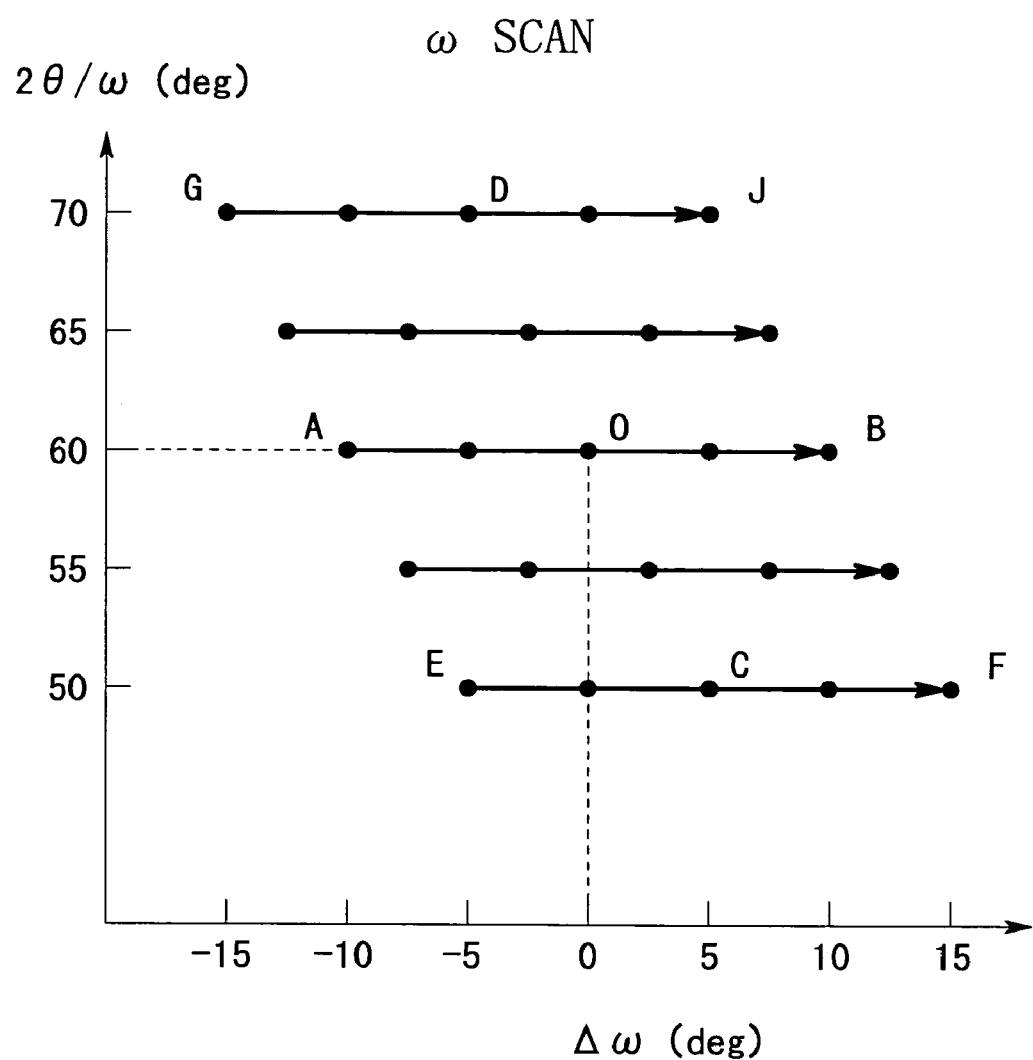
FIG. 13 is a graph expressing the measuring range shown in FIG. 12 in the coordinate system made of Δω-axis and 2θ/ω-axis.

The second method is that the scan range for ω is first produced with the absolute-angle-designated range kept as it is as shown in FIG. 12 and thereafter the scan range is amended as shown in FIG. 7 so as to be acquired. For example, the scan range for ω is first produced as shown in FIG. 12; the ω scan range takes a minus-five-degree shift at 50 degrees in 2θ/ω; the ω scan range takes a minus-2.5-degree sift at 55 degrees in 2θ/ω; and so forth. Generally speaking the ω scan range takes a shift by a half of the difference between the target point in 2θ/ω, which is 60 degrees, and the current point in 2θ/ω. This method would be eventually equivalent to the conversion of the absolute-angle-designated range into the relative-angle-designated range.

The method according to the present invention is not limited to the embodiment described above but may be applied to the reciprocal-space mapping measurement in the in-plane diffraction for example. The in-plane reciprocal-space mapping is disclosed in the second publication mentioned above and the angular scan about the in-plane rotation of the sample in the second publication would operate similarly to the ω scan in the embodiment described above. That is to say, the measuring regions of the reciprocal-space mapping are different from each other between the relative-angle-designated and the absolute-angle-designation regarding the in-plane rotation angle of the sample. Also in this case, the absolute-angle-designated range can be converted into the relative-angle-designated range in setting the measuring range, expecting the same advantage as the embodiment above.

What is claimed is:

1. In a method of obtaining reciprocal-space mapping of X-ray diffraction having the steps of:
    preparing a first angular variable and a second angular variable both of which define a relative angular location among an incident X-ray, a sample and a diffracted X-ray;
    changing the first angular variable so that a magnitude of a scattering vector of X-ray diffraction is changed with a direction of the scattering vector kept constant to produce a first condition-change;
    changing the second angular variable so that the direction of the scattering vector is changed with the magnitude kept constant to produce a second condition-change;
    combining the first condition-change with the second condition-change so as to make a plurality of the scattering vectors which are included in a desired measuring region surrounding a predetermined target point in a reciprocal space; and
    carrying out X-ray diffraction measurement for the plurality of the scattering vectors so as to make the reciprocal-space mapping,
    a method of setting measuring ranges of the reciprocal-space mapping comprising the steps of:
    (a) determining whether a designated range of the second angular variable is a relative-angle-designated range on a basis of the target point or an absolute-angle-designated range;
    (b) acquiring the relative-angle-designated range as an allowable range of the second angular variable when the determining step determines the relative-angle-designated range, or converting the absolute-angle-designated range into the relative-angle-designated range and acquiring the thus-converted relative-angle-designated range as an allowable range of the second angular variable when the determining step determines the absolute-angle-designated range; and
    (c) acquiring any one of a relative-angle-designated range and an absolute-angle-designated range as an allowable range of the first angular variable.

2. A method according to claim 1, wherein the determining step is carried out using a condition-setting screen which includes a selection region having a relative-angle check place and an absolute-angle check place, the two check places being selectively marked by an operator.

3. A method according to claim 1, wherein
    assuming that an incident angle of the incident X-ray to a surface of the sample is referred to as ω, and a diffraction angle of the diffracted X-ray to the incident X-ray referred to as 2θ,
    the first angular variable is an angular variable, which is referred to as 2θ/ω, with which the 2θ and the ω are changed in a interlocking fashion so as to keep the direction of the scattering vector unchanged, and
    the second angular variable is the ω.

4. A method according to claim 3, wherein the determining step is carried out using a condition-setting screen which includes a selection region having a relative-angle check place and an absolute-angle check place, the two check places being selectively marked by an operator.

5. A method according to claim 4, wherein
    the condition-setting screen includes a measuring-range item which has the selection region and a numerical-value entry region, and
    the numerical-value entry region has two entry boxes for the 2θ/ω and two entry boxes for the ω.

6. A method according to claim 5, wherein the condition-setting screen further includes:
    a center-point item for entry of the target point of the measuring region in 2θ/ω and ω;
    a scan-direction item for selection between a 2θ/ω scan and an ω scan;
    a scan-method item for selection between a continuous scan and a stepwise scan; and
    a measuring-interval item for entry of angular intervals in 2θ/ω and ω with which measurement operations are carried out.

* * * * *